United States Patent
Kamen et al.

(10) Patent No.: US 11,227,687 B2
(45) Date of Patent: *Jan. 18, 2022

(54) SYSTEM, METHOD, AND APPARATUS FOR COMMUNICATING DATA

(71) Applicant: DEKA Products Limited Partnership, Manchester, NH (US)

(72) Inventors: Dean Kamen, Bedford, NH (US); John M. Kerwin, Manchester, NH (US); Todd A. Ballantyne, Amherst, NH (US); Frederick Morgan, Canton, MA (US); Jason A. Demers, Manchester, NH (US); John J. Biasi, Groton, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 152 days.

This patent is subject to a terminal disclaimer.

(21) Appl. No.: 15/992,547

(22) Filed: May 30, 2018

(65) Prior Publication Data
US 2018/0278676 A1    Sep. 27, 2018

Related U.S. Application Data

(60) Division of application No. 14/135,809, filed on Dec. 20, 2013, now Pat. No. 10,044,791, which is a
(Continued)

(51) Int. Cl.
*G16H 40/67* (2018.01)
*H04L 29/08* (2006.01)
(Continued)

(52) U.S. Cl.
CPC ............. *G16H 40/67* (2018.01); *H04L 67/10* (2013.01); *G16H 40/63* (2018.01); *H04L 41/06* (2013.01); *H04L 43/10* (2013.01)

(58) Field of Classification Search
None
See application file for complete search history.

(56) References Cited

U.S. PATENT DOCUMENTS 6,776,152 B2    8/2004    Gray et al.
8,380,126 B1    2/2013    Ma et al.
(Continued)

FOREIGN PATENT DOCUMENTS

CN    1643870 A    7/2005
JP    07245625 A    9/1995
(Continued)

OTHER PUBLICATIONS

Tanenbaum A S Ed—Tanenbaum A S: "Computer Networks" Jan. 1, 1988, Computer Networks, Englewood Cliffs, Prentice Hall, US, pp. 1-27, XP002023239.
(Continued)

*Primary Examiner* — Brian Whipple
(74) *Attorney, Agent, or Firm* — James D. Wyninegar, Jr.

(57) ABSTRACT

A system includes first and second hubs. The first hub is configured to communicate data with a medical device through a Local Area Network and package the data into at least one application-layer packet. The second hub is configured to receive the at least one application-layer packet from the first hub operatively through at least one cellular network.

27 Claims, 4 Drawing Sheets

Related U.S. Application Data continuation-in-part of application No. 13/723,253, filed on Dec. 21, 2012, which is a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/333,574 is a continuation-in-part of application No. 13/011,543, filed on Jan. 21, 2011, now abandoned, said application No. 14/135,809 is a continuation-in-part of application No. 13/723,239, filed on Dec. 21, 2012, now Pat. No. 10,108,785, which is a continuation-in-part of application No. 13/333,574, filed on Dec. 21, 2011, now Pat. No. 10,453,157, which is a continuation-in-part of application No. 13/011,543, filed on Jan. 21, 2011, now abandoned, said application No. 13/723, 239 is a continuation-in-part of application No. PCT/US2011/066588, filed on Dec. 21, 2011, said application No. 14/135,809 is a continuation-in-part of application No. 13/723,242, filed on Dec. 21, 2012, now Pat. No. 10,911,515, and a continuation-in-part of application No. 13/900,655, filed on May 23, 2013, which is a continuation-in-part of application No. 13/480,444, filed on May 24, 2012, now Pat. No. 9,717,834, and a continuation-in-part of application No. PCT/US2012/000257, filed on May 24, 2012, said application No. 14/135,809 is a continuation-in-part of application No. PCT/US2013/042350, filed on May 23, 2013, which is a continuation-in-part of application No. 13/480,444, filed on May 24, 2012, now Pat. No. 9,717,834, and a continuation-in-part of application No. PCT/US2012/000257, filed on May 24, 2012.

(60) Provisional application No. 61/740,474, filed on Dec. 21, 2012, provisional application No. 61/578,649, filed on Dec. 21, 2011, provisional application No. 61/578,658, filed on Dec. 21, 2011, provisional application No. 61/578,674, filed on Dec. 21, 2011, provisional application No. 61/651,322, filed on May 24, 2012, provisional application No. 61/679,117, filed on Aug. 3, 2012, provisional application No. 61/297,544, filed on Jan. 22, 2010.

(51) Int. Cl.
*H04L 12/24* (2006.01)
*H04L 12/26* (2006.01)
*G16H 40/63* (2018.01)

(56) References Cited

U.S. PATENT DOCUMENTS

| | | |
|---|---|---|
| D728,779 S | 5/2015 | Sabin et al. |
| D735,319 S | 7/2015 | Sabin et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg |
| 9,724,465 B2 | 8/2017 | Peret et al. |
| 9,724,466 B2 | 8/2017 | Peret et al. |
| 9,724,467 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| D801,519 S | 10/2017 | Sabin et al. |
| 9,789,247 B2 | 10/2017 | Kamen et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |
| D805,183 S | 12/2017 | Sabin et al. |
| 9,856,990 B2 | 1/2018 | Peret et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,479 S | 5/2018 | Sabin et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,044,791 B2 | 8/2018 | Kamen et al. |
| 10,082,241 B2 | 9/2018 | Janway et al. |
| 10,088,346 B2 | 10/2018 | Kane et al. |
| 10,108,785 B2 | 10/2018 | Kamen et al. |
| 10,113,660 B2 | 10/2018 | Peret et al. |
| 10,126,267 B2 | 11/2018 | Blumberg, Jr. |
| 10,185,812 B2 | 1/2019 | Kamen et al. |
| 10,202,970 B2 | 2/2019 | Kamen et al. |
| 10,202,971 B2 | 2/2019 | Kamen et al. |
| 10,220,135 B2 | 3/2019 | Kamen et al. |
| 10,228,683 B2 | 3/2019 | Peret et al. |
| 10,242,159 B2 | 3/2019 | Kamen et al. |
| 10,245,374 B2 | 4/2019 | Kamen et al. |
| 10,265,463 B2 | 4/2019 | Biasi et al. |
| 10,288,057 B2 | 5/2019 | Kamen et al. |
| 10,316,834 B2 | 6/2019 | Kamen et al. |
| D854,145 S | 7/2019 | Collins |
| 10,380,321 B2 | 8/2019 | Kamen et al. |
| 10,391,241 B2 | 8/2019 | Desch et al. |
| D860,437 S | 9/2019 | Collins |
| 10,426,517 B2 | 10/2019 | Langenfeld et al. |
| 10,436,342 B2 | 10/2019 | Peret et al. |
| 10,453,157 B2 | 10/2019 | Kamen et al. |
| 10,468,132 B2 | 11/2019 | Kamen et al. |
| 10,471,402 B2 | 11/2019 | Demers et al. |
| 10,478,261 B2 | 11/2019 | Demers et al. |
| 10,488,848 B2 | 11/2019 | Peret et al. |
| 10,561,787 B2 | 2/2020 | Kamen et al. |
| 10,563,681 B2 | 2/2020 | Kamen et al. |

(56) References Cited

U.S. PATENT DOCUMENTS

| | | | |
|---|---|---|---|
| 10,571,070 B2 | 2/2020 | Gray et al. |
| 10,655,779 B2 | 5/2020 | Janway et al. |
| 10,670,182 B2 | 6/2020 | Janway et al. |
| 10,718,445 B2 | 7/2020 | Yoo |
| 10,722,645 B2 | 7/2020 | Kamen et al. |
| 10,739,759 B2 | 8/2020 | Peret et al. |
| 10,753,353 B2 | 8/2020 | Kamen et al. |
| 10,761,061 B2 | 9/2020 | Wilt et al. |
| 10,839,953 B2 | 11/2020 | Kamen et al. |
| 10,844,970 B2 | 11/2020 | Peret et al. |
| D905,848 S | 12/2020 | Sloss et al. |
| 10,857,293 B2 | 12/2020 | Kamen et al. |
| 10,872,685 B2 | 12/2020 | Blumberg, Jr. et al. |
| 10,876,868 B2 | 12/2020 | Kane et al. |
| 10,894,638 B2 | 1/2021 | Peret et al. |
| 10,911,515 B2 | 2/2021 | Biasi et al. |
| D917,045 S | 4/2021 | Gray |
| 10,994,074 B2 | 5/2021 | Blumberg, Jr. et al. |
| 11,024,409 B2 | 6/2021 | Kamen et al. |
| 11,024,419 B2 | 6/2021 | Kamen et al. |
| 2001/0037366 A1* | 11/2001 | Webb ............. A61N 1/37282 709/204 |
| 2004/0059205 A1 | 3/2004 | Carlson et al. |
| 2005/0065817 A1* | 3/2005 | Mihai ............. A61B 5/0002 705/2 |
| 2005/0232151 A1 | 10/2005 | Chapweske et al. |
| 2007/0156450 A1 | 7/2007 | Roehm et al. |
| 2007/0253021 A1* | 11/2007 | Mehta ............. A61B 5/0002 358/1.15 |
| 2009/0240120 A1 | 9/2009 | Mensinger et al. |
| 2011/0002223 A1 | 1/2011 | Gross |
| 2011/0021140 A1 | 1/2011 | Binier |
| 2011/0125515 A1* | 5/2011 | Lytle ............. G06Q 10/10 705/2 |
| 2011/0172550 A1 | 7/2011 | Martin et al. |
| 2011/0313789 A1 | 12/2011 | Kamen et al. |
| 2012/0185267 A1 | 7/2012 | Kamen |
| 2012/0229271 A1 | 9/2012 | Davis |
| 2012/0259978 A1 | 10/2012 | Petersen et al. |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0314083 A1 | 4/2015 | Blumberg, Jr. et al. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0049029 A1 | 2/2018 | Kumar et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2018/0224012 A1 | 8/2018 | Peret et al. |
| 2018/0228964 A1 | 8/2018 | Blumberg, Jr. et al. |
| 2018/0252359 A1 | 9/2018 | Janway et al. |
| 2018/0278676 A1 | 9/2018 | Kamen et al. |
| 2019/0009018 A1 | 1/2019 | Kamen et al. |
| 2019/0033104 A1 | 1/2019 | Kane et al. |
| 2019/0041362 A1 | 2/2019 | Blumberg, Jr. |
| 2019/0134298 A1 | 5/2019 | Kamen et al. |
| 2019/0139640 A1 | 5/2019 | Kamen et al. |
| 2019/0154026 A1 | 5/2019 | Kamen et al. |
| 2019/0170134 A1 | 6/2019 | Kamen et al. |
| 2019/0175821 A1 | 6/2019 | Kamen et al. |
| 2019/0179289 A1 | 6/2019 | Peret et al. |
| 2019/0189272 A1 | 6/2019 | Kamen et al. |
| 2019/0219047 A1 | 7/2019 | Kamen et al. |
| 2019/0249657 A1 | 8/2019 | Kamen et al. |
| 2019/0298913 A1 | 10/2019 | Biasi et al. |
| 2019/0316948 A1 | 10/2019 | Karol et al. |
| 2019/0328964 A1 | 10/2019 | Desch et al. |
| 2019/0341146 A1 | 11/2019 | Kamen et al. |
| 2019/0365421 A1 | 12/2019 | Langenfeld et al. |
| 2020/0025305 A1 | 1/2020 | Peret et al. |
| 2020/0051190 A1 | 2/2020 | Kamen et al. |
| 2020/0054823 A1 | 2/2020 | Baier et al. |
| 2020/0066388 A1 | 2/2020 | Kamen et al. |
| 2020/0070113 A1 | 3/2020 | Demers et al. |
| 2020/0078127 A1 | 3/2020 | Demers et al. |
| 2020/0171241 A1 | 6/2020 | Kamen et al. |
| 2020/0173469 A1 | 6/2020 | Kamen et al. |
| 2020/0182400 A1 | 6/2020 | Gray et al. |
| 2020/0278078 A1 | 9/2020 | Janway et al. |
| 2020/0292127 A1 | 9/2020 | Janway et al. |
| 2020/0347949 A1 | 11/2020 | Yoo |
| 2020/0371497 A1 | 11/2020 | Peret et al. |
| 2020/0386220 A1 | 12/2020 | Kamen et al. |
| 2020/0393414 A1 | 12/2020 | Wilt et al. |
| 2021/0023296 A1 | 1/2021 | Langenfeld et al. |
| 2021/0062929 A1 | 3/2021 | Peret et al. |
| 2021/0065867 A1 | 3/2021 | Kamen et al. |
| 2021/0085858 A1 | 3/2021 | Kamen et al. |
| 2021/0098102 A1 | 4/2021 | Blumberg, Jr. et al. |
| 2021/0125719 A1 | 4/2021 | Peret et al. |

(56) References Cited

U.S. PATENT DOCUMENTS

FOREIGN PATENT DOCUMENTS

| | | | |
|---|---|---|---|
| JP | 2000224223 A | 8/2000 |
| JP | 2001022656 A | 1/2001 |
| JP | 2003023413 A | 1/2003 |
| JP | 2005109849 A | 4/2005 |
| JP | 2005215996 A | 8/2005 |
| JP | 2006211380 A | 8/2006 |
| JP | 2006260325 A | 9/2006 |
| JP | 4661440 B2 | 3/2011 |
| WO | WO2007047128 A1 | 4/2007 |
| WO | WO2013095459 A9 | 6/2013 |
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

OTHER PUBLICATIONS

Tanenbaum A S Ed—Tanenbaum A S: "Computer Networks" Jan. 1, 1996, Computer Networks, Prentice-Hall International, London; GB, pp. 183-190, XP002220024, ISBN: 978-0-13-394248-4.

International Preliminary Report on Patentability dated Jun. 23, 2015, received in International patent application No. PCT/US2013/076886, 10 pgs.

Invitation to Pay Additional Fees and, Where Applicable, Protest Fee dated May 9, 2014, received in International patent application No. PCT/US2013/076886, 8 pgs.

International Search Report dated Jul. 14, 2014, received in International patent application No. PCT/US2013/076886, 7 pgs.

Communication of the Substantive Examination Result dated Jun. 22, 2017, from the Mexican Institute of Industrial Property for application MX/a/2015/008050, pgs.

Notice of Reason for Rejection from Japanese Patent Office for Patent Application No. 2015-549773, dated Nov. 21, 2017.

U.S. Appl. No. 61/740,474, filed Dec. 21, 2012.

PCT/US2013/76886, Dec. 20, 2013, WO/2014/100571A1.

U.S. Appl. No. 14/135,809, filed Dec. 20, 2013, US20140195639A1.

Lee, Insup & Sokolsky, Oleg & Chen, Sanjian & Hatcliff, John & Jee, Eunkyoung & Kim, Baekgyu & King, Andrew & Mullen-Fortino, Margaret & Park, Soojin & Roederer, Alexander & Venkatasubramanian, Krishna. (2012). Challenges and Research Directions in Medical Cyber-Physical Systems. Proceedings of the IEEE. 100. 10.1109/JPROC.2011.2165270.

Decision to refuse a European Patent application, in EPO Application No. 13 824 562.6-1126, Oral Proceedings Jun. 29, 2021, dated Aug. 10, 2021.

Provisional minutes of for oral proceeding before the Examing Division for EPO Application No. 13 824 562.6-1126, Oral Proceedings Jun. 29, 2021, issued Sep. 8, 2021.

\* cited by examiner

SYSTEM, METHOD, AND APPARATUS FOR COMMUNICATING DATA

CROSS-REFERENCES TO RELATED APPLICATIONS

This Application is a Divisional Application of U.S. patent application Ser. No. 14/135,809, filed Dec. 20, 2013 and entitled System, Method, and Apparatus for Communicating Data, now U.S. Publication No. US-2014-0195639-A1, published Jul. 10, 2014 which claims the benefit of U.S. Provisional Patent Application Ser. No. 61/740,474, filed Dec. 21, 2012 and entitled System, Method, and Apparatus for Communicating Data, which is hereby incorporated herein by reference in its entirety.

U.S. patent application Ser. No. 14/135,809 is also a Continuation-In-Part Application of U.S. patent application Ser. No. 13/723,253, filed Dec. 21, 2012 and entitled System, Method, and Apparatus for Electronic Patient Care, now U.S. Publication No. US-2013-0191413-A1, published Jul. 25, 2013, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253 is a Continuation-In-Part of U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/333,574 is a Continuation-In-Part Application of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility, both of which are hereby incorporated herein by reference in their entireties.

U.S. patent application Ser. No. 14/135,809 is also Continuation-In-Part Application of U.S. patent application Ser. No. 13/723,239, filed Dec. 21, 2012 and entitled System, Method, and Apparatus for Electronic Patient Care, now U.S. Publication No. US-2013-0297330-A1, published Nov. 7, 2013, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239 claims priority to, benefit of, and is also a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part Application of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application Ser. No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, now International Publication No. WO 2013/095459, published Sep. 12, 2013, each of which is hereby incorporated herein by reference in their entireties.

U.S. patent application Ser. No. 14/135,809 is also a Continuation-In-Part Application of U.S. patent application Ser. No. 13/723,242, filed Dec. 21, 2012 and entitled System, Method, and Apparatus for Electronic Patient Care, now U.S. Publication No. US-2013-0317753-A1, published Nov. 28, 2013, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

U.S. patent application Ser. No. 14/135,809 is also a Continuation-In-Part Application of U.S. Ser. No. 13/900,655, filed May 23, 2013 and entitled System, Method, and Apparatus for Electronic Patient Care, now U.S. Publication No. US-2013-0317837-A1, published Nov. 28, 2013 which claims priority to and the benefit of U.S. Provisional Patent Application Ser. No. 61/651,322, filed May 24, 2012 and entitled System, Method, and Apparatus for Electronic Patient Care, both of which are hereby incorporated herein by reference in their entireties.

U.S. patent application Ser. No. 13/900,655 is also a Continuation-In-Part Application which claims priority to and the benefit of the following:

U.S. patent application Ser. No. 13/480,444, filed May 24, 2012 and entitled Blood Treatment Systems and Methods, now U.S. Publication No. US-2013-0037485-A1, published Feb. 14, 2013; and PCT Application Serial No. PCT/US12/00257, filed May 24, 2012 and entitled Blood Treatment Systems and Methods, now International Publication No. WO/2012/161744, published Nov. 29, 2012.

U.S. patent application Ser. No. 14/135,809 is also a Continuation-In-Part Application of PCT Application Serial No. PCT/US13/42350, filed May 23, 2013 and entitled System, Method, and Apparatus for Electronic Patient Care, which claims priority to and the benefit of U.S. Provisional Patent Application Ser. No. 61/651,322, filed May 24, 2012 and entitled System, Method, and Apparatus for Electronic Patient Care, both of which are hereby incorporated herein by reference in their entireties.

PCT Application Ser. No. PCT/US13/42350 is also a Continuation-In-Part Application which claims priority to and the benefit of the following:

U.S. patent application Ser. No. 13/480,444, filed May 24, 2012 and entitled Blood Treatment Systems and Methods, now U.S. Publication No. US-2013-0037485-A1, published Feb. 14, 2013; and PCT Application Serial No. PCT/US12/00257, filed May 24, 2012 and entitled Blood Treatment Systems and Methods, now International Publication No. WO/2012/161744, published Nov. 29, 2012.

U.S. patent application Ser. No. 14/135,809 may also be related to one or more of the following patent applications filed on Dec. 21, 2012, all of which are hereby incorporated herein by reference in their entireties:

Nonprovisional application for System, Method, and Apparatus for Clamping, Ser. No. 13/723,238;

Nonprovisional application for System, Method, and Apparatus for Dispensing Oral Medications, Ser. No. 13/723,235;

PCT application for System, Method, and Apparatus for Dispensing Oral Medications, Ser. No. PCT/US12/71131;

Nonprovisional application for System, Method, and Apparatus for Estimating Liquid Delivery, Ser. No. 13/724,568;

Nonprovisional application for System, Method, and Apparatus for Infusing Fluid, Ser. No. 13/725,790;

PCT application for System, Method, and Apparatus for Infusing Fluid, Ser. No. PCT/US12/71490;

Nonprovisional application for System, Method, and Apparatus for Monitoring, Regulating, or Controlling Fluid Flow, Ser. No. 13/723,244;

PCT application for System, Method, and Apparatus for Monitoring, Regulating, or Controlling Fluid Flow, Ser. No. PCT/US12/71142;

Nonprovisional application for System, Method, and Apparatus for Estimating Liquid Delivery, Ser. No. 13/723,251; and PCT application for System, Method, and Apparatus for Estimating Liquid Delivery, Ser. No. PCT/US12/71112.

The present application may also be related to one or more of the following patent applications, all of which are hereby incorporated herein by reference in their entireties:

U.S. Provisional Patent Application Ser. No. 61/738,447, filed Dec. 18, 2012 and entitled System, Method, and Apparatus for Detecting Air in a Fluid Line Using Active Rectification;

U.S. patent application Ser. No. 13/840,339, filed Mar. 15, 2013 and entitled Apparatus for Infusing Fluid;

PCT Application Serial No. PCT/US13/32445, filed Mar. 15, 2013 and entitled Apparatus for Infusing Fluid;

U.S. patent application Ser. No. 13/833,432, filed Mar. 15, 2013 and entitled Syringe Pump and Related Method;

U.S. patent application Ser. No. 13/836,497, filed Mar. 15, 2013 and entitled System and Apparatus for Electronic Patient Care;

U.S. patent application Ser. No. 13/833,712, filed Mar. 15, 2013 and entitled System, Method, and Apparatus for Clamping;

U.S. patent application Ser. No. 13/834,030, filed Mar. 15, 2013 and entitled System, Method, and Apparatus for Monitoring, Regulating, or Controlling Fluid Flow; and PCT application for System, Method, and Apparatus for Communicating Data, filed Dec. 20, 2013, Ser. No. PCT/US13/76886.

BACKGROUND

Field of Disclosure

The present disclosure relates to communicating data. More particularly, the present disclosure relates to a system, method, and apparatus for communicating data, such as between medical devices and one or more enterprise servers.

Description of Related Art

In some instances, one or more medical devices may be used by a particular patient to treat an acute or chronic ailment. These medical devices may include electronic control circuitry that executes software algorithms that ensure the patient is properly being treated, the treatment is not outside of accepted predetermined norms, and that the medical device itself is operating within acceptable parameters.

Because each particular treatment prescribed for a patient may be unique and/or involve the use of multiple devices, outside databases and computer systems (e.g., an enterprise system) may be used to provide these devices with information related to the patient and/or the patient's treatment regime. The information may be used to facilitate the interaction of multiple medical devices during a treatment session. Various communication technologies may be used to achieve one or more device-to-server communication links.

SUMMARY

In an embodiment of the present disclosure, a method of communication includes: communicating data from a medical device to a first hub via a Local Area Network; packaging the data from the medical device into at least one packet, wherein a packet of the at least one packet includes a header; communicating the at least one packet over a network through at least one communications channel of the first hub; communicating an alarm from the first hub to a medical device when an alarm condition occurs within the first hub, if necessary. The method may be performed within an application layer (e.g., the packets may be application-layer level packets) or in any other layer or combination of layers. A first communications channel of the at least one communications channel may be over a first cellular network, e.g., plain old telephone service ("POTS") or broadband. A second communications channel of the at least one communications channel may be over a second cellular network, e.g., plain old telephone service ("POTS") or broadband. The first hub may be associated with an identification value (e.g., a serial number), a patient, a medical device, and/or a treatment.

The act of communicating the data from the medical device to the first hub via the Local Area Network may be an act of receiving the data by the first hub via the Local Area Network from the medical device.

In yet another embodiment of the present disclosure, the method may further include the act of encrypting the data (e.g., by the first hub and/or by the medical device). The method may include the act of receiving the at least one packet over the network through at least one communications channel by a second hub, and the act of decrypting the data within the second hub.

The method may include the act of determining a time parameter, e.g., a date and/or a time. A satellite system signal may be used to determine the time parameter. Additionally or alternatively, the method may use a cellular time server, a Network Identity and Time Zone ("NITZ") server, a time sever, etc. to determine the time parameter. The method may include the act of adding the time parameter to the header of the packet. The method may perform the act of determining whether the time parameter within the header of the packet meets a first predetermined criterion.

The method may further include an act of adding a sequence number to the header of the packet; reassembly the data using the sequence number of the header of the packet; determining an error-detection code corresponding to at least a portion of the packet; adding the error-detection code to the header of the packet; and/or determining whether the at least a portion of the packet is error free by examining the error-detection code within the header of the packet.

In yet another embodiment of the present disclosure, the method may include the acts of determining whether at least one of the packet and the data satisfies a second predetermined criterion; and/or communicating an acknowledgment character corresponding to at least one of the packet and the data to the first hub if the second predetermined criterion is satisfied.

In yet another embodiment of the present disclosure, the method may include the acts of receiving the at least one packet over the network through the at least one communications channel by a second hub; and/or routing the data from the second hub to at least one enterprise server (e.g., a transaction server) or analytic server.

The act of packaging the data from the medical device into at least one packet may include packaging the data into the packet and into another packet. The packet may include a header, and the another packet may include another header. The method may further include the acts of: adding a first sequence number to the header of the packet; and adding a second sequence number to the another header of the another packet.

The act of communicating the at least one packet over a network through one of at least one communications channel of the first hub may include the acts of: communicating the packet over a first communications channel of the at least one communications channel of the first hub; and communicating the another packet over a second communications channel of the at least one communications channel of the first hub. The method may include receiving the packet and the another packet; and reassembling the data in accordance with the first sequence number of the packet and the second sequence numbers of the another packet.

In yet some additional embodiments of the present disclosure, the method may include the acts of encrypting, by the medical device (or the first or second hub), the data prior to communicating the data from the medical device to the first hub via the Local Area Network; receiving the at least one packet over the network through one or more communications channels (e.g., two communications channels) by a second hub; routing the data from the second hub to an enterprise server; and/or decrypting, by the enterprise server, the data for processing by the enterprise server.

In yet another embodiment of the present disclosure, a hub includes a local area network interface component, first and second system-on-module ("SOM") modules, and a processor. The local area network interface component is configured to communicate data with a medical device. The first SOM is configured to interface with a first communications channel, and the second SOM is configured to interface with a second communications channel. The first communications channel may be a first cellular network, and the second communications channel may be a second cellular network. The processor is configured to package the data from the medical device into at least one packet. A packet of the at least one packet includes a header, and the processor is further configured to operatively communicate with one of the first and second SOMs to communicate the at least one packet over one of the first and second communications channel. The processor may be further configured to associate the hub with one of an identification value, a patient, a medical device, and a treatment. Additionally, alternatively, or optionally, the processor may be configured to encrypt the data.

In yet another embodiment of the present disclosure, the processor is further configured to add a time parameter to the header of the packet. The time parameter may include a date and/or a time. The hub may include a satellite system component, and the processor is configured to add the time parameter to the header using a time determined by a satellite system using the satellite system component. In some embodiments, the hub uses a cellular time servicer, Network Identity and Time Zone ("NITZ"), a time sever, etc. to determine the time.

In yet another embodiment of the present disclosure, the processor is further configured to add a sequence number to the header of the packet. The sequence number may be configured for reassembling the data using the sequence number of the header of the packet.

In yet another embodiment of the present disclosure, the processor is further configured to add an error-detection code corresponding to at least a portion of the packet to the header of the packet. The error-detection code is an error-correction code.

The processor may be configured to package the data into the packet and into another packet, wherein the packet includes the header and the another packet includes another header.

In yet another embodiment of the present disclosure, the hub further includes a failsafe +bus. The failsafe bus may be configured to signal a medical device coupled thereto when a fault condition of the hub or of the communications link has occurred.

In yet another embodiment of the present disclosure, the hub further includes an alarm bus. The alarm bus may be configured to signal a medical device coupled thereto when an alarm condition of the hub has occurred or of the communications link if the link quality has degraded.

In yet another embodiment of the present disclosure, the hub further includes a plain-old-telephone-service component. The processor may be configured to route the packet through the plain-old-telephone-service ("POTS") when the first and second communications channels are unavailable. For example, the hub may call 911 if an emergency condition has been determined to exist. In some embodiments, the hub may download voice data from a server to audible broadcast instructions, for example. The serial number of the hub may be used to determine which language the voice message will be in among a list of possible languages.

In yet another embodiment of the present disclosure, a system includes first and second hubs. The first hub is configured to communicate data with a medical device through a Local Area Network and package the data into at least one application-layer packet. The second hub is configured to receive the at least one application-layer packet from the first hub operatively through at least one cellular network. The first hub may be configured to encrypt the data and the second hub may be configured to decrypt the data.

The first hub may communicate the at least one application-layer packet through first and second cellular networks of the at least one cellular network. The second hub may be configured to reassemble the data from the at least one application-layer packet. The first hub may be configured to load balance the transmission of the at least one application-layer packet between the first and second cellular networks or to transmit data redundantly utilizing both of the first and second cellular networks. For example, each pack may be sent twice, once using the first cellular network and once using the second cellular network. The enterprise system may compare the received packets and determine if they contain identical data. That is, the data within the two packets may not be identical if the data in one or both of the packets become corrupted during transmission.

The system may further include an enterprise server. The medical device may be configured to encrypt the data and the second hub may be configured to route the data to the enterprise server, and the enterprise server may be configured to decrypt the data.

In yet another embodiment of the present disclosure, the first hub includes a global positioning component configured to determine a time parameter using at least one global positioning signal. The first hub adds the time parameter to a header of an application-layer packet of the at least one application-layer packet, and the second hub is configured to determine if the time parameter meets predetermined criterion.

The second hub may include another global positioning component configured to determine another time parameter using at least one global positioning signal. The second hub may be configured to determine if the time parameter meets the predetermined criterion as a function of the another time parameter.

In another embodiment of the present disclosure, the at least one application-layer packet includes a first application-layer packet, and the first hub is configured to add an error-detection code corresponding to at least a portion of the first application-layer packet. The second hub may be configured to determine if the at least the portion of the first application-layer packet is error free using the error-detection code. The error-detection code may be an error-correction code. wherein the second hub is further configured to correct, if necessary, an error of the at least the portion of the first application-layer packet.

The at least one application-layer packet may include a first application-layer packet, and the second hub is configured communicate an acknowledgement to the first hub if the first application-layer packet satisfies predetermined criterion.

In another embodiment of the present disclosure, the system further includes an enterprise server. The medical device is configured to encrypt the data. And, the second hub is configured to route the data to the enterprise server such that the enterprise server is configured to decrypt the data. When data is written to the enterprise server, an acknowledgement may be sent back to the first hub and/or to the medical device.

In some embodiments, the at least one application-layer packet includes first and second application-layer packets. The first hub is configured to add a first sequence number to a first header of the first application-layer packet and to add a second sequence number to a second header of the second application-layer packet. The second hub is configured to reassembly the data in accordance with the first and second sequence numbers. The first hub may be configured to communicate the first application-layer packet over a first cellular network of the at least one cellular network. The first hub is configured to communicate the second application-layer packet over a second cellular network of the at least one cellular network.

In yet another embodiment of the present disclosure, the first hub includes an alarm bus component configured to provide an alarm condition signal. The medical device is operatively coupled to the first hub to receive the alarm condition signal. The medical device is configured to provide at least one mitigation when an alarm condition is received via the alarm condition signal.

In yet another embodiment of the present disclosure, the first hub includes a failsafe component configured to provide a fatal, error-condition signal. The medical device is operatively coupled to the first hub to receive the fatal-error, condition signal. The medical device is configured to operate independently of the hub when a fatal-error, condition exists via the fatal-error-condition signal.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
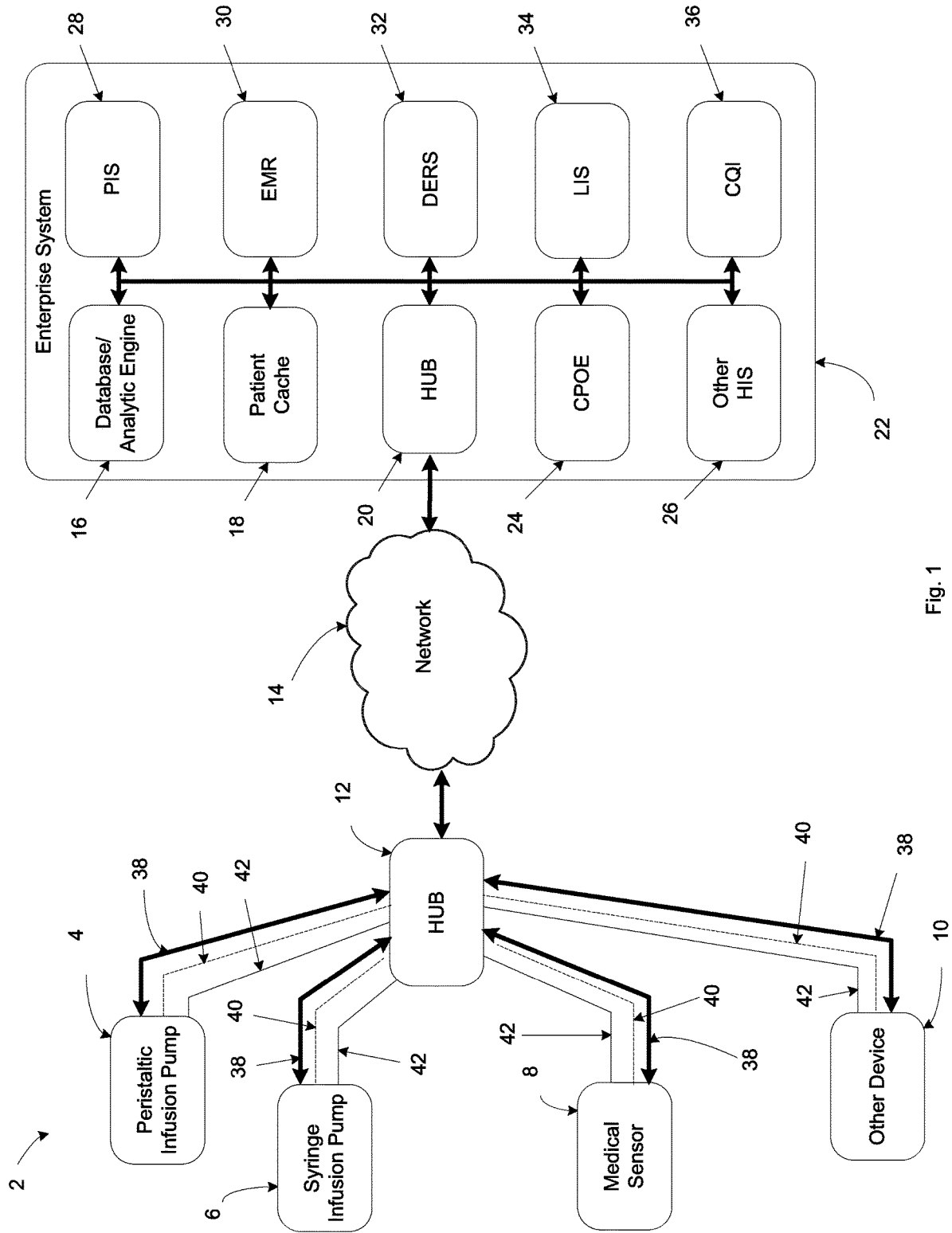
FIG. 1 shows a block diagram of a system for communicating data in accordance with an embodiment of the present disclosure.

FIG. 1 shows a block diagram of a system 2 for communicating data in accordance with an embodiment of the present disclosure. The system includes hubs 12, 20 that communicate with each other over a network 14. The first hub 12 is operatively coupled to medical devices 4, 6, 8, 10. That is, the first hub 12 is in operative communication with one or more of the medical devices 4, 6, 8, 10. In some embodiments, multiple hubs 12 may be used (e.g., one device for each hub).

The hub 12 may include requirements that must be met prior to allowing a medical device to connect to it. Additionally or alternatively, the hub 12 may require that the link quality between the first and second hubs 12, 20 meet predetermined criteria prior to communicating data therebetween. The hub 12 may communicate the link quality between the hubs 12, 20 to one or more of the medical devices 4, 6, 8, 10.

The second hub 20 is operatively coupled to various enterprise servers 16, 18, 24, 26, 28, 30, 32, 34, 36 of the enterprise system 22. The enterprise system 22 may be implemented by one or more servers, may be a server farm, may be implemented as one or more virtual servers, and/or may be a software programs implemented by one or more processors. The enterprise various enterprise servers 16, 18, 24, 26, 28, 30, 32, 34, 36 may be transaction servers.

The hubs 12, 20 may communicate data between the medical devices 4, 6, 8, 10 and the enterprise servers 16, 18, 24, 26, 28, 30, 32, 34, 36 such that the data is seamlessly communicated therebetween. For example, in some specific embodiments, the hubs 12, 20 may wrap data into packets such that the data communicated between the medical devices 4, 6, 8, 10 and the enterprise servers 16, 18, 24, 26, 28, 30, 32, 34, 36 is communicated between each other as if they were on the same Local Area Network. In some specific embodiments, the data may be wrapped into one or more packets at the application layer, e.g., the application layer of the Open Systems Interconnection model (ISO/IEC 7498-1) ("OSI model"), the entire contents of which are hereby incorporated by reference. In some embodiments, the data may be wrapped in one or more layers of any known communications standard known to one of ordinary skill in the relevant art, e.g., an application layer of another model. In some additional embodiments, the data may be wrapped in one or more layers of any packet model known in the art including the OSI model. In yet some additional embodiments, the wrapping of the one or more packets may be done at a combination of the application, presentation, and session layers of the OSI model and/or the presentation and session layers may not be implemented. The hub 20 may route the data from one of the medical devices 4, 6, 8, 10 to one of the enterprise servers 16, 18, 24, 26, 28, 30, 32, 34, 36.

The hubs 12, 20 may communicate with each other in a synchronous manner or in a non-synchronous manner. Additionally, the hubs 12, 20 may communicate a heart beat signal to each other. For example, each of the hubs 12, 20 may send out a signal indicating that is operating properly to the other one of the hubs 12, 20 periodically at predetermined intervals. If one of the hubs 12, 20 does not receive a heartbeat signal (or, in some embodiments, any signal) from the other hub within a predetermined amount of time, the hub that has not received a heartbeat signal within the predetermined amount of time may (1) request a heartbeat signal be sent, (2) determine that the other hub has malfunction and take appropriate predetermined mitigation measures, (3) signal that an alarm has occurred on the alarm bus, and/or (4) signal that the heartbeat signal has not received within the predetermined amount of time via the fail safe bus.

As the hubs 12, 20 communicate with each other, the receiving hub (i.e., receiving the data) may send an acknowledgment to the transmitting hub. In some specific embodiments, the acknowledgment may also include a sequence number or other packet identifier.

The hub 12 and/or the medical devices 4, 6, 8, 10 may have an associated identification value that gives the data from the medical devices 4, 6, 8, 10 predetermined access to one or more of the enterprise servers 16, 18, 24, 26, 28, 30, 32, 34, 36. Additionally, alternatively, or optionally, the associated identification may be associated with access to various subsets of services or data within each of the enterprise servers 16, 18, 24, 26, 28, 30, 32, 34, 36.

In some embodiments, the hub 12 may be associated with a patient, with one or more of the medical devices 4, 6, 8, 10, and/or with a treatment regime.

Each of the medical devices 4, 6, 8, 10 or the first hub 12 may communicate its capability, its configuration and/or annunciate any alarms or faults to one or more of the enterprise servers 16, 18, 24, 26, 28, 30, 32, 34, 36 or to the second hub 20.

The hubs 12, 20 may wrap the data into one or more packets such that each packet includes a header. The header may include: (1) a sequence number; (2) an error-detection code, such as an error-correction code; and/or (3) one or more time parameters, such as a date and/or a time.

The sequence numbers may be used to reassemble the data. For example, the hub 12 may break up the data into a plurality of packets each being assigned a sequence number. The hub 12 may communicate the plurality of packets through a first cellular network via a first cell modem 64 and a second cellular network via a second cell modem 84 (see FIG. 2). The first and second cellular networks may be 2G networks, 3G networks, 4G networks, an LTE network, or a wifi-to-internet connection. The hub 12 may also perform load balancing. When the data reaches the second hub 20, the second hub 20 reassembles the data using the sequence numbers.

An error-detection code may be used, such as, for example, an error-correction code which can detect and correct errors contained within the data. Any error-detection code may be used, such as cyclic redundancy check ("CRC"), a checksum, a hash sum, a parity bit, a parity word, MD5, etc. The first hub 12 may add the error-detection code to the header of the one or more packets prior to transmitting them to the second hub 20; the second hub 20 may determine if the data has one or more errors using the error-detection code, and, in some specific embodiments, the second hub 20 corrects the data (or vice versa when transmitting form the second hub 20 to the first hub 12).

The first hub 12 and/or the second hub 20 may add a time parameter, such as a date/time stamp to the headers prior to communication to the other one of the hubs 12, 20. The receiving hub of the hubs 12, 20 may determine if the date/time stamp meets a predetermined criterion, such as a requirement that the packet be received within a predetermined period of time. The receiving hub of the hubs 12, 20 may compare the date/time stamp with an internally determined time parameter to determine whether the packet was received within the predetermined period of time since the date/time was determined by the transmitting hub of the hubs 12, 20. The hubs 12, 20 may use a time reference determined using one or more satellites of a satellite system. In some embodiments, the satellite may be part of a global navigation satellite system. For example, signals from one or more satellites of the Global Positioning System constellation, the Globalnaya Navigatsionnaya Sputnikovaya Sistema ("GLONASS") constellation, the Indian Regional Navigational Satellite System ("IRNSS") constellation, the BeiDou Navigation System constellation, the Galileo constellation, etc. may be used to determine the time parameter.

The data may be encrypted by the transmitting one of the hubs 12, 20 and likewise decrypted by the receiving one of the hubs 12, 20. Additionally, alternatively, or optionally, the medical devices 4, 6, 8, 10 may encrypt the data prior to sending the data to the enterprise servers 16, 18, 24, 26, 28, 30, 32, 34, 36, which in turn, decrypt the data when received; likewise, the enterprise servers 16, 18, 24, 26, 28, 30, 32, 34, 36, may encrypt the data prior to sending the data to the medical devices 4, 6, 8, 10, which in turn, decrypt the data when received. Any encryption may be used, such as public-key encryption, symmetric-key encryption, session-key encryption, Advanced Encryption Standard ("AES"), Data Encryption Standard ("DES"), Triple DES, Hypertext Transfer Protocol Secure ("HTTPS"), Transport Layer Security ("TLS"), Secure Sockets Layer ("SSL"), an encryption standard of Federal Information Processing Standard ("FIPS"), some other encryption technology known to one of ordinary skill in the art, or some combination thereof.

The medical devices 4, 6, 8, 10 or the hub 12 may communicate to the enterprise system 22 various information, such as: (1) its status, such as if the device is operating or is inoperable; (2) its location; (3) its configuration, such as its software version, its hardware version or its capabilities; (4) the available bandwidth; and/or (5) requirements of the medical device. In some embodiments, the medical devices can only connect to the hub 12 when the available bandwidth exceeds a predetermined threshold.

The medical devices medical devices 4, 6, 8, 10 may communicate to the enterprise system 22 its software and/or firmware version number in order to obtain updates. The updates may be verified and/or validated using any known technology, such as encryption verification. The enterprise system 22 may use the version number to send to one or more of the medical devices 4, 6, 8, 10 updated software and/or updated firmware if the version number received is not the latest version.

Additionally, alternatively, or optionally, the hub 12 may communicate to the enterprise system 22 its software and/or firmware version number to obtain updates. The enterprise system 22 may use the version number to send the hub 12 updated software and/or updated firmware if the version number received is not the latest version.

In some embodiments, software may be stored in the hub 12, which is used to update software in one or more of the medical devices 4, 6, 8, 10. The hub 12 may request that the version number of the firmware and/or software that resides on one or more medical devices 4, 6, 8, 10 be sent to the hub 12. The hub 12 can then determine whether the medical devices 4, 6, 8, 10 have the latest software or firmware version by reference to an internal database or via reference to version information received from the enterprise system 22. The hub 12 may download the software or firmware from the enterprise system 22. The hub 12 may load the software into the medical devices 4, 6, 8, 10, which may run any known algorithms to update software and/or firmware. For example, a new version of the firmware may be loaded into one of the medical devices 4, 6, 8, 10 and thereafter verified. The medical device (4, 6, 8, or 10) may then verify the new firmware and the "switch" the medical device to use the new firmware (e.g., via a pointer, for example).

Additionally, in some embodiments, the medical devices 4, 6, 8, 10 and/or the hub 12 communicate to the enterprise system 22 alerts, alarms, faults, log information or other diagnostic information for recordation by the continuous quality improvement ("CQI") server 36.

The hubs 12, 20 communicate over the network 14, which may include any type of network. For example, the hub 12 may communicate data over one or more cellular phone networks which route data over the internet to the hub 20. In some embodiments, the hubs 12, 20 communicate via a wireless-internet link, a wired-internet link, a broadband link, using POTS, or other know communication technology known to one of ordinary skill in the art. In some embodiments, the cellular network provider may couple the enterprise system 22 directly to a data connection configured to receive data over the one or more cellular networks.

The medical devices 4, 6, 8, 10 are in operative communication with the hub 12 thorough a LAN connection 38, an alarm bus 40, and a failsafe bus 42. The LAN connection 38 may use any local area network technology and protocol, and the hub 12 may support multiple LAN technologies and protocols. Each of the medical devices 4, 6, 8, 10 may use different local area network technologies from each other.

The alarm bus 40 may be implemented by a wire that is normally held in a high state (e.g., at 5 volts) by the hub 12. When the hub 12 determines that an internal alarm has occurred, the hub 12 may signal that an alarm condition within the hub 12 has occurred via an alarm condition signal (e.g., by setting the wire to 0 volts). That is, the alarm bus 40 can be used to communicate that an alarm condition has occurred. When each of the medical devices 4, 6, 8, 10 determines that an alarm condition has occurred, each of the medical devices 4, 6, 8, 10 may implement at least one mitigation action, such as by lowering the LAN connection's 38 bandwidth, using an internal cellular connection to communication with the network 14, or other mitigation. In some embodiments, the medical devices 4, 6, 8, 10 may enter into a safe mode when an alarm condition is reported by the hub 12 to the medical devices 4, 6, 8, 10 (or, in some embodiments, when a medical device of the medical devices 4, 6, 8, 10 detects an internal alarm). In some embodiments, the alarm bus 40 is a digital communications bus which communications information about the alarm to the medical devices 4, 6, 8, 10.

In some embodiments, the alarm bus 40 sets an alarm state as a function of the network's 14 or the hub's 12 capability or performance. The each of the medical devices 4, 6, 8, 10 may communicate to the hub 12 a list of conditions in which the hub 12 should communicate to the requesting medical devices 4, 6, 8, 10 when an alarm condition has occurred.

The hub 12 may also includes a failsafe bus 42. The failsafe bus 42 coupled between the hub 12 and the medical devices 4, 6, 8, 10 provides a fatal, error-condition signal that indicates when a fatal, error condition has occurred within the hub 12. The signal may be a "high" value (e.g., 5 Volts) that transitions to a "low" value (e.g., 0 volts) to indicate that an fatal, error condition exists within the hub 12. The medical devices 4, 6, 8, 10 may be configured to operate independently of the hub when the fatal-error, condition exists as indicated by the fatal-error-condition signal. In some embodiments, the fatal-error, conditions may be defined by the hub 12 and/or by a medical device coupled to the hub 12. In some embodiments, the failsafe bus 42 is a digital communications bus which communications information about the fatal, error-condition to the medical devices 4, 6, 8, 10.

The peristaltic infusion pump 4 may be any kind of peristaltic infusion pump 4, such as a finger-type pump or a rotary infusion pump. The syringe infusion pump 6 may be any syringe pump driven by a motor, for example. The other device 10 may be any medical device. In some embodiments, the pumps 4, 6 (or the other device 10) receive feedback from the medical sensor 8.

The medical sensor 8 may be any patient or environment sensor, such as a blood pressure sensor, a temperature sensor, a blood glucose meter, and a heart rate monitor, pulse oximeter, for example.

In one specific embodiment, the medical sensor 8 is a blood-pressure cuff or a pill dispenser that provides feedback to one or more medical devices 4, 6, 10. The information about blood pressure of compliance of taking a pill may be used to adjust the flow rate of a pump 4 or 6. In some embodiments, the feedback to sent to a doctor via the enterprise system 22 (e.g., an electronic message may be sent to a tablet or smart phone, for example).

In yet another embodiment, the medical sensor 10 may be a pulse oximeter which provides feedback to the peristaltic infusion pump 4. If the peristaltic infusion pump 4 determines that the patient's blood oxygen saturation falls below a predetermined threshold and/or the patient's heart rate fall below a predetermined threshold, the infusion pump 4 may stop fluid flow. In some embodiments, the hub 12 shuts off the peristaltic infusion pump 4 if the patient's blood oxygen level is below a predetermined threshold or the patient's heart rate is below a threshold.

In one embodiment, the other device 10 generates oxygen for a patient. The medical sensor 8 may be a pulse oximeter which provides to the other device 10 the blood-oxygen saturation of the patient as feedback. The other device 10 may generate oxygen to ensure that the patient's blood oxygen saturation level is at least a predetermined level.

In yet another embodiment, the other device 10 may initiate a "call in" predetermined conditions are satisfied. For example, if the other device 10 is a pill dispenser, the pill dispenser may send an alarm or an alert to a doctor in the event of noncompliance. A provider may alter the next dose delivered by the pill dispenser via a user interface of the tablet or smart phone.

In some embodiments of the present disclosure, the hub 12 routes information from one or more medical sensors 8 to one or more of the devices 4, 8, 10. This closed-loop configuration may form a real-time feedback system. In some specific embodiments, the one or more medical sensors 8 may form a close-loop configuration with the one or more of the devices 4, 8, 10 as long as: (1) a communication latency is below a predetermined threshold; (2) the wireless signal noise is below a predetermined threshold; and/or (3) a predetermined amount of bandwidth is available, or some combination thereof. The hub 12, in some embodiments, may signal that an alarm or a fatal condition has occurred to the medical devices 4, 6, 8, 10 when one or more of these conditions are not met. The alarm or alert conditions may be communicated to the enterprise system 22. In some embodiments, the hubs 12, 20, and/or the medical devices 4, 6, 8, or 10 may go into a failsafe/operative mode in response to an alarm or an alert condition.

In some embodiments, a hierarchy of responses may be programmed within one of the medical devices 4, 6, 8, 10 or the hub 12 based upon which alarm or alert occurs, and/or how much time has elapsed without any user interaction with the hub 12 or one of the medical devices 4, 6, 8, 10. A caregiver can program the hierarchy of responses, e.g., from a generic framework. The hierarchy of responses may be validated by the enterprise system 22, in some embodiments.

The enterprise system 22 may include one or more of a database/analytic engine, a patient cache 18, the hub 20, a CPOE 24, other HIS 26, A PIS 28, an EMR 30, a DERS 32, a LIS 34, and/or a CQI 36.

The database/analytic engine 16 collects data from the hub 12 and/or the devices 4, 6, 8, 10 to determine trends and/or one or more statistics. The database/analytic engine 16 can interface with one or more of the servers 18, 24, 26, 28, 30, 32, 34, 36 to generate one or more reports for users interfacing into the database/analytic engine 16.

The hub 12 and/or one of the devices 4, 6, 8, 10 may determine a patient's identification (e.g., using a barcode scanner, an RFID scanner, or manually by entering in the patient's ID into a screen). Patient data regarding the treatment may be loaded into a patient cache 18, which can instruct the hub 12 and/or one of the medical devices 4, 6, 8, 10 what to do with the data. The patient cache 18 may be implemented in memory, such as in RAM or in hard drive memory. The patient cache 18 may load the data from any one of the servers 24, 26, 28, 30, 32, 34, 36 to provide faster responses for patient data from the hub 12 and/or the devices 4, 6, 8, 10 or to organize data differently.

The enterprise system 22 may also include a computerized physician order entry ("CPOE") server 24. The CPOE 24 can receive orders (e.g., over the internet) for treatments and/or prescriptions for a particular patient. The CPOE 24 may be compared with the medication scanned in by the pumps 4, 6 to determine if it is correct for the identified patient.

The CPOE 24 can receive care algorithms from a caregiver. The care algorithm may include rules regarding which feedback to use, which set points to achieve, and/or which drugs to administer. The caregiver may interface into the CPOE 24 using a computer terminal, a tablet, a Smartphone, or other user interface. The CPOE 24 and/or the enterprise system 22 may validate the care algorithm.

The enterprise system 22 may also include a pharmacy information system ("PIS") server 28, an electronic medical records ("EMR") server 30, and a laboratory information system ("LIS") server 34, in which the devices 4, 6, 8, 10 can access. The enterprise system 22 can also include any other Hospital Information System ("HIS") server 26.

The enterprise system 22 may also include a drug error reduction system ("DERS") server 32. The DERS server 32 may include information that allows one or more devices 4, 6, 8, 10 to determine if the therapy (e.g., delivery of a medication via an IV bag coupled to the peristaltic infusion pump 4) is safe. For example, an IV bag may include a barcode affixed thereto. The infusion pump 4 may scan the barcode of the IV bag and communicate that information to, for example, the PIS 28 to determine the contents of the IV bag and, with the DERS 32, determine if the medication and treatment parameters are safe 3 for the identified patient or for any patient (via hard limits).

The enterprise system 22 may also include a continuous quality improvement ("CQI") server 36. The CQI server 36 receives messages from the medical devices 4, 6, 8, 10 that describe the operation of the device. The CQI messages sent to the CQI server 36 may be used to monitor the fleet of the medical devices 4, 6, 8, 10 to identify any issues or problems with them.

In some embodiments of the present disclosure, one of the medical devices 4, 6, 8, 10 can use resources of another device of the medical devices 4, 6, 8, 10. In some embodiments, the medical devices 4, 6, 8, 10 and/or the hub 12 may operate as a mesh network.

A user interfaced into the enterprise system 22 can monitor the hub 12 and/or the medical devices 4, 6, 8, 10. The hub 12 and/or the medical devices 4, 6, 8, 10 may transmit an image (e.g., a JPEG) of the screen to a user interface coupled to the enterprise system 22 or may communicate audio as well (e.g., from a microphone). HTML5 may be used and/or telepresence may be used as well so that a user may monitor the hub 12 and/or the medical devices 4, 6, 8, 10 using a user interface coupled to the enterprise system 22.

Figure 2:
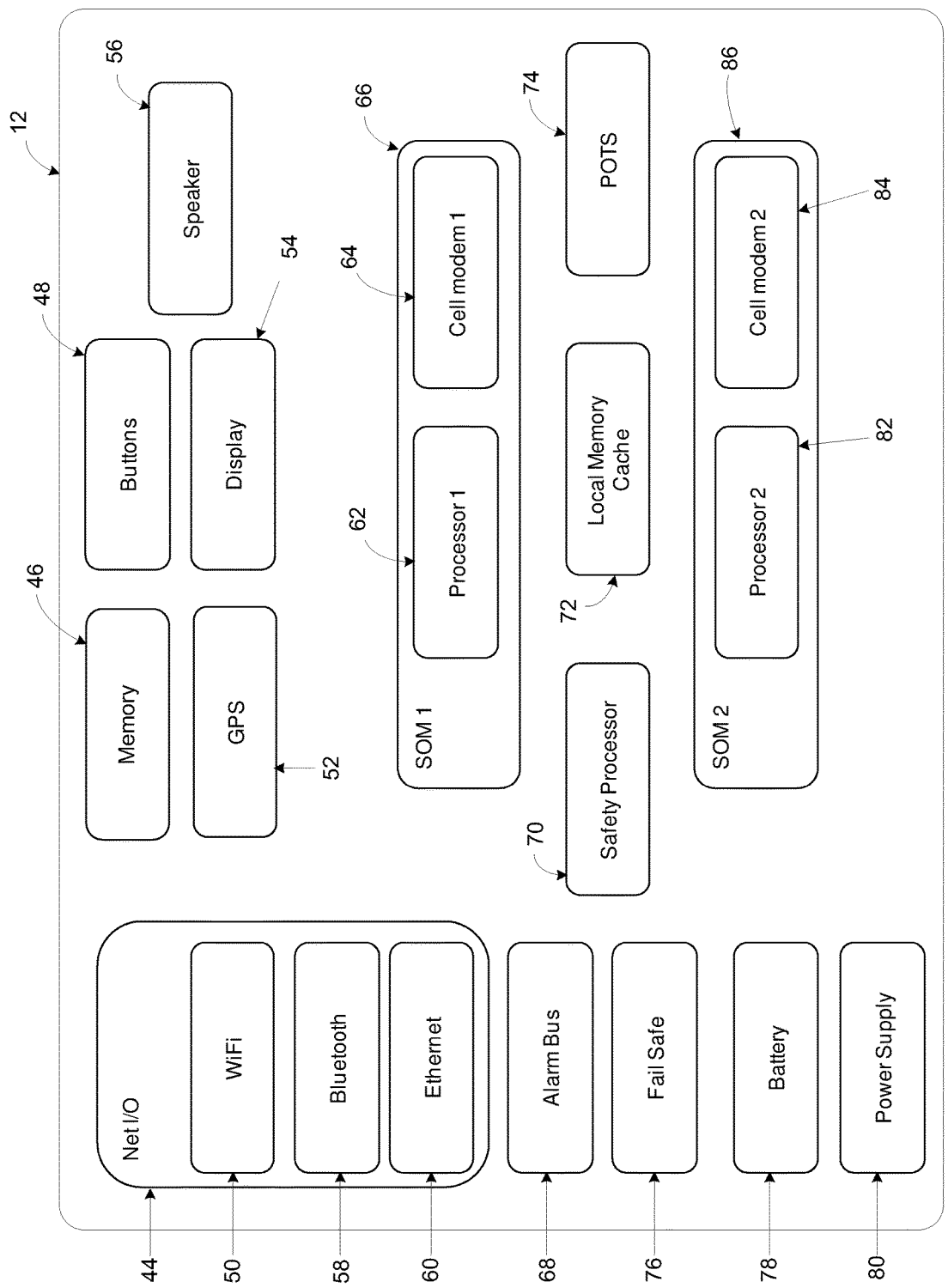
FIG. 2 shows a block diagram of a hub of the system of FIG. 1 in accordance with an embodiment of the present disclosure.

FIG. 2 shows a block diagram of a hub 14 of the system of FIG. 1 in accordance with an embodiment of the present disclosure. In some specific embodiments, the hub 20 of FIG. 1 may use the same hardware as the hub 14.

The hub 12 includes a LAN interface 44, an alarm bus 68, a failsafe bus 76, a battery 78, a power supply 80, a memory 46, buttons 48, a GPS component 52, a display 54, a speaker 56, and first and second system-on-module ("SOM") modules 66, 86, a safety processor 70, a local memory cache 72, and plain old telephone service ("POTS") 74.

The hub 12 may be powered by power supply circuitry 80 which converts AC outlet power to DC power which supplies power to the internal circuitry of the hub 12. The power supply 80 can also charge the battery 78. In the event of power loss from the power source that supplies the power supply circuitry 80, the battery 78 supplies power to the hub 12. Multiple batteries 78 and/or multiple power supplies 80 may be used to provide additional redundancy, in some specific embodiments.

The LAN interface 44 includes a WiFi transceiver 50, a Bluetooth transceiver 58, and an Ethernet interface 60. In some embodiments, the LAN interface 44 uses any wired- or wireless-protocol or standard known to one of ordinary skill in the relevant art. A medical device can communicate with the hub 12 via the LAN interface 44.

The data received via the LAN interface 44 is buffered into a memory 46. Either an interrupt and/or an algorithm can select the data within the memory 46 for transmission. The data is packaged into one or more packets and transmitted over the first SOM 66 and/or via the second SOM 86. The first SOM 66 includes a processor 62 and a cellular network modem 64 for transmitting the packets over a first cellular network. The second SOM 86 also includes a processor 82 that can transmit one or more packets over a second cellular modem 84 over a second cellular network. The SOM modules 66 and 86 may perform load balancing. The POTS 74 may be used when communication through both of the cellular networks is unavailable. In some embodiments, the POTS 74 may call an emergency number if an emergency condition has been determined to exist (e.g., call "911" in the United States). In yet some additional embodiments, the hub 12 calls a service number if an alarm, alert or fault condition has been determined to exists (to report them) and the cellular networks are unavailable.

The modules 77 and 86 may use the local memory cache 72 to communicate between each other and/or to coordinate operations. The local memory cache 72 may be part of the memory 46 or may be separate therefrom. In some embodiments of the present disclosure the local memory cache 72 is a memory location for the medical devices 4, 6, 8, 10 (e.g., to communicate between each other). The local memory cache 72 may fill with data for transmission to the enterprise system 22 when the link to the network 14 is unavailable, for example.

In some embodiments, the data within the local memory cache 72 may be periodically reported to the enterprise system 22 or in accordance with predefined rules or with rules communicated to the hub 12 from the enterprise system 22 (e.g., via a user at a terminal of the enterprise system 22).

The packets may be formed at the application-layer level. The packets may each include a header. The header may include: (1) position information; (2) time information as determined by a Global Positioning System receiver 52; (3) error-detection codes; (4) sequence numbers; (5) or other information.

The hub 12 also includes an alarm bus 68 (i.e., an alarm bus component). The alarm bus is configured to provide an alarm condition signal to one or more medical devices. The medical devices may be operatively coupled to the hub to receive an alarm condition signal from the alarm bus 68. The signal may be a "high" value (e.g., 5 Volts) that transitions to a "low" value (e.g., 0 Volts) to indicate that an alarm condition exists within the hub. The medical device may engage in at least one mitigation action when an alarm condition is received via the alarm condition signal. For example, the medical device may require add error-correction codes to the data sent to the hub 12. The safety processor 70 may determine when an alarm condition exists and communicates that condition to the alarm bus 68. In some embodiments, the alarm conditions may be defined by the hub 12 and/or by a medical device coupled to the hub 12. The safety processor 70 may use the local memory cache 72. The safety processor 70 may monitor the hub 12 independently of the operation of the processors 62, 82 of the SOMS 66, 86. For example, the safety processor 70 may not rely on the use of the processors 62, 82 and may operate as a watchdog to them, in some specific embodiments.

The hub 12 also includes a failsafe bus 78. The failsafe bus 76 provides a fatal, error-condition signal that indicates when a fatal, error condition has occurred within the hub 12. The signal may be a "high" value (e.g., 5 Volts) that transitions to a "low" value (e.g., 0 volts) to indicate that a fatal, error-condition exists within the hub. The medical device may be configured to operate independently of the hub when a fatal-error, condition exists as indicated by the fatal-error-condition signal. The safety processor 70 may determine when a fatal, error-condition exists and communicates that condition to the alarm bus 68. In some embodiments, the fatal-error, conditions may be defined by the hub 12 and/or by a medical device coupled to the hub 12. In some embodiments, the hubs 12, 20, and/or the medical devices 4, 6, 8, or 10 may go into a failsafe/operative mode in response to an alarm or an alert condition.

In the event when communication between a medical device (e.g., devices 4, 6, 8, 10 of FIG. 1) and the enterprise system 22 fails (See FIG. 1), the medical devices 4, 6, 8, 10 and the hub 12 may record all information within an internal memory for reporting to the enterprise system 22 when communications are restored. Additionally or alternatively, a computer may be coupled to the medical devices 4, 6, 8, 10 or the hub 12 to download the data (e.g., via a RS-232 or USB connection).

A user can input setting into the hub 12 using the buttons 48, and/or the display 54. The hub 12 may provide audible feedback through the speaker 56 or the display 54. The hub 12 may communicate sound over a LAN 38 connection to one or more of the devices 4, 6, 8, 10 for playing sound using an internal speaker.

The speaker 56 may be used to announce what the hub is doing, such as "attempting to connect to a server" or "I'm calling phone number 1-234-567-1829." In some embodiments, the speaker 56 may be used to audibly state any error conditions, faults, and/or alarms. The messages may be prerecorded and may be selected based upon the determined language of the patient. The messages may be transmitted to the hub 12 from the enterprise system 22 (see FIG. 1). The determined language of the patient may be based upon the location of the hub 12 (e.g., determined via the GPS signal), from the patient's records or from any other way known to one or ordinary skill in the relevant art. The prerecorded voice may be a voice of a familiar provider to the patient.

In addition to the audio component of the messages, the messages may also include a prerecorded video that is displayed on the display 54. The audio and video may be synchronized with each other.

The speaker 56 and the display 54 may be used to provide training videos to the user regarding the operation or configuration of the hub 12 and/or the medical devices 4, 6, 8, 10 (see FIG. 1). Additionally, in some embodiments, speaker 56 and the display 54 may be used to provide health notes and/or CPR training.

Figure 3A:
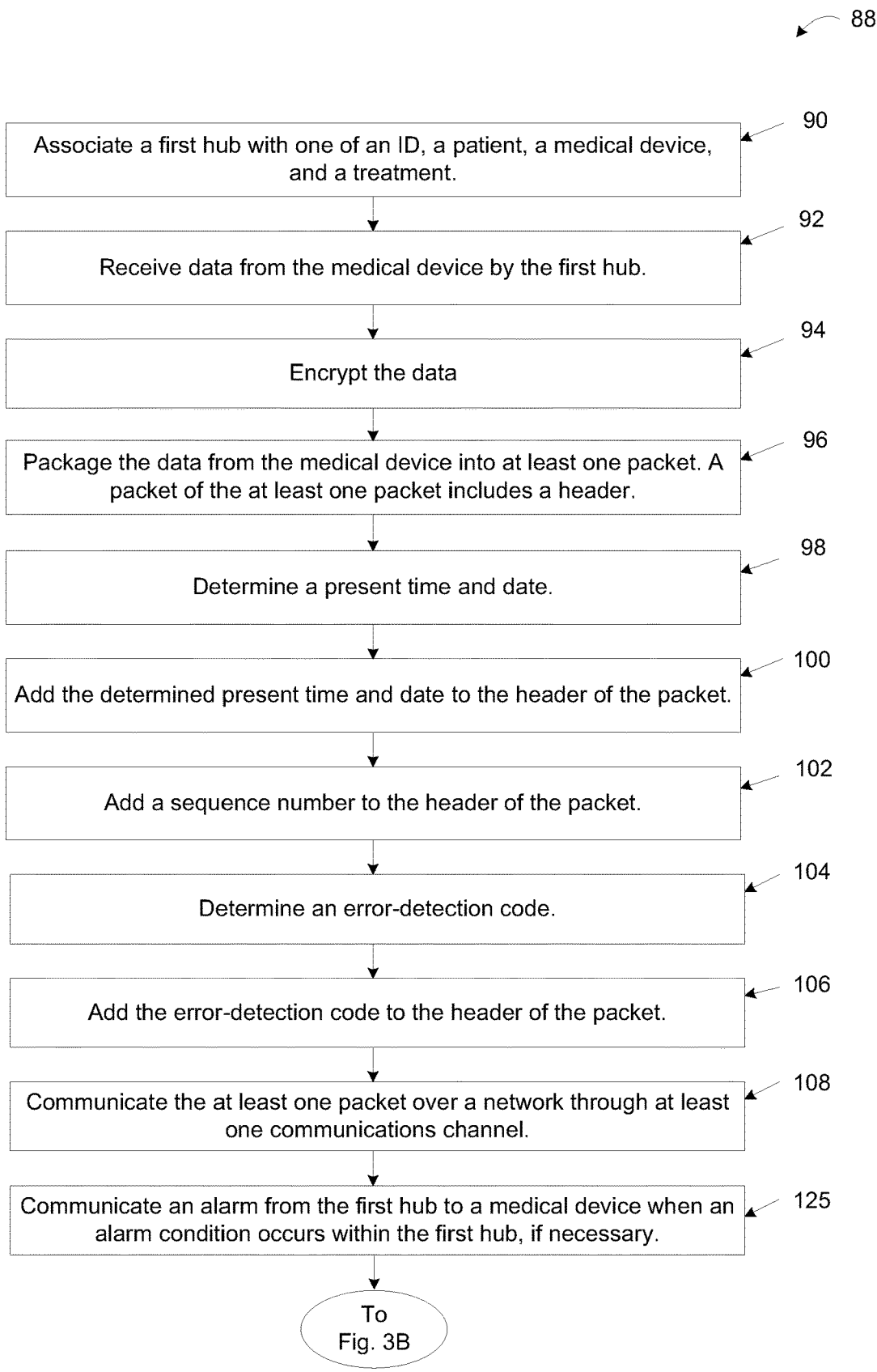
FIGS. 3A-3B show a flow chart diagram illustrating a method for communicating data in accordance with an embodiment of the present disclosure.
Figure 3B:
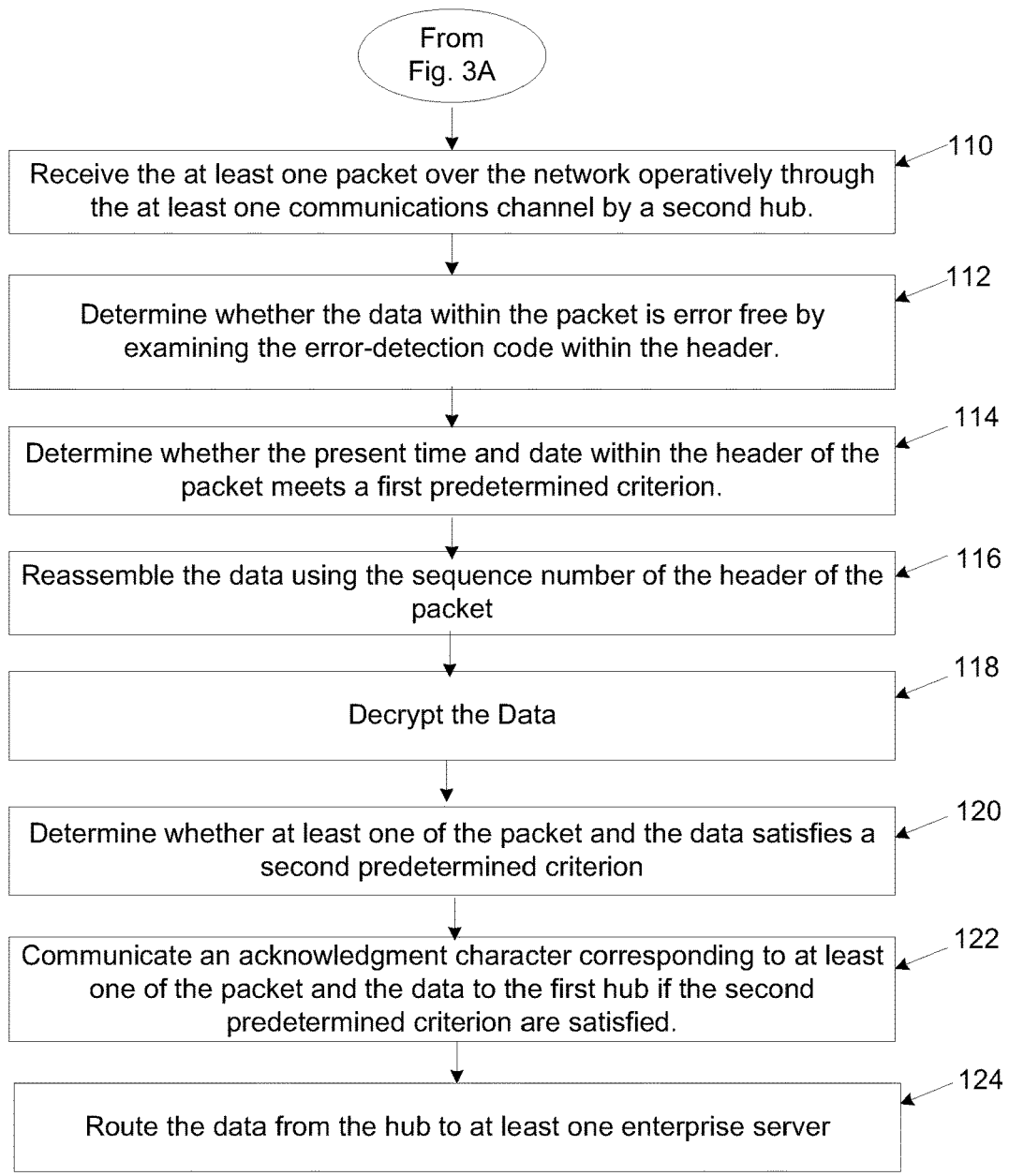

FIGS. 3A-3B show a flow chart diagram 88 illustrating a method for communicating data in accordance with an embodiment of the present disclosure.

Act 90 associates a first hub with one of an ID, a patient, a medical device, and a treatment. Act 92 receives data from the medical device by the first hub (which may be stored in a local cache). Act 94 encrypts the data. Act 96 packages the data from the medical device into at least one packet. A packet of the at least one packet includes a header.

Act 98 determines a present time and date. Act 100 adds the determined present time and date to the header of the packet. Act 102 adds a sequence number to the header of the packet. Act 104 determines an error-detection code. Act 106 adds the error-detection code to the header of the packet. Act 108 communicates the at least one packet over a network through at least one communications channel. Act 125 communicates an alarm from the first hub to a medical device when an alarm condition occurs within the first hub, if necessary. For example, if the alarm is a fatal alarm. The alarm may be communicated using the alarm bus 68 of FIG. 2, in some embodiments.

Act 110 receives the at least one packet over the network operatively through the at least one communications channel by a second hub. Act 112 determines whether the data within the packet is error free by examining the error-detection code within the header. Act 114 determines whether the present time and date within the header of the packet meets a first predetermined criterion. Act 116 reassembles the data using the sequence number of the header of the packet.

Act 118 decrypts the Data. Act 120 determines whether at least one of the packet and the data satisfies a second predetermined criterion. Act 122 communicates an acknowledgment character corresponding to at least one of the packet and the data to the first hub if the second predetermined criterion is satisfied. The second predetermined criterion may be, for example, that the data has been logged into a database. Act 124 routes the data from the hub to at least one enterprise server. One or both of the hubs may monitor the communications channel(s), e.g., using heartbeat signals.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A method of communication, the method comprising:
   communicating data from a medical device to a first hub via a Local Area Network;
   packaging the data from the medical device into at least one packet, wherein a packet of the at least one packet includes a header;
   communicating the at least one packet over a network through at least one communications channel of the first hub;
   communicating an alarm from the first hub to a medical device over an alarm wire bus when an alarm condition occurs within the first hub;
   communicating a fatal-error fault condition of the hub over a failsafe bus to the medical device; and
   executing at least mitigation by the medical device in response to the alarm.

2. The method according to claim 1, wherein the act of communicating the data from the medical device to the first hub via the Local Area Network is receiving the data by the first hub via the Local Area Network from the medical device.

3. The method according to claim 1, wherein a first communications channel of the at least one communications channel is over a first cellular network, and a second communications channel of the at least one communications channel is over a second cellular network.

4. The method according to claim 1, further comprising associating the first hub with an identification value.

5. The method according to claim 1, further comprising associating the first hub with a patient.

6. The method according to claim 1, further comprising associating the first hub with a medical device.

7. The method according to claim 1, further comprising associating the first hub with a treatment.

8. The method according to claim 1, further comprising encrypting the data.

9. The method according to claim 8, further comprising:
   receiving the at least one packet over the network through at least one communications channel by a second hub; and
   decrypting the data within the second hub.

10. The method according to claim 1, further comprising determining a time parameter.

11. The method according to claim 10, wherein the time parameter includes one of a date and a time.

12. The method according to claim 10, wherein a satellite system signal is used to determine the time parameter.

13. The method according to claim 10, further comprising adding the time parameter to the header of the packet.

14. The method according to claim 13, further comprising determining whether the time parameter within the header of the packet meets a first predetermined criterion.

15. The method according to claim 1, further comprising adding a sequence number to the header of the packet.

16. The method according to claim 15, further comprising reassembling the data using the sequence number of the header of the packet.

17. The method according to claim 1, further comprising determining an error-detection code corresponding to at least a portion of the packet.

18. The method according to claim 17, further comprising adding the error-detection code to the header of the packet.

19. The method according to claim 18, determining whether the at least a portion of the packet is error free by examining the error-detection code within the header of the packet.

20. The method according to claim 1, further comprising:
determining whether at least one of the packet and the data satisfies a first predetermined criterion; and
communicating an acknowledgment character corresponding to at least one of the packet and the data to the first hub if the second predetermined criterion is satisfied.

21. The method according to claim 1, further comprising:
receiving the at least one packet over the network through the at least one communications channel by a second hub; and
routing the data from the second hub to at least one enterprise server.

22. The method according to claim 1, wherein the act of packaging the data from the medical device into at least one packet includes packaging the data into the packet and into another packet, wherein the packet includes the header and the another packet includes another header.

23. The method according to claim 22, further comprising:
adding a first sequence number to the header of the packet; and
adding a second sequence number to the another header of the another packet.

24. The method according to claim 23, wherein the act of communicating the at least one packet over a network through one of at least one communications channel of the first hub, comprises:
communicating the packet over a first communications channel of the at least one communications channel of the first hub; and
communicating the another packet over a second communications channel of the at least one communications channel of the first hub.

25. The method according to claim 24, further comprising:
receiving the packet and the another packet; and
reassembling the data in accordance with first sequence number of the packet and the second sequence numbers of the another packet.

26. The method according to claim 1, further comprising encrypting, by the medical device, the data prior to communicating the data from the medical device to the first hub via the Local Area Network.

27. The method according to claim 26, further comprising:
receiving the at least one packet over the network through at least one communications channel by a second hub;
routing the data from the second hub to an enterprise server; and
decrypting, by the enterprise server, the data for processing by the enterprise server.

* * * * *